United States Patent
King et al.

(10) Patent No.: US 6,620,446 B2
(45) Date of Patent: *Sep. 16, 2003

(54) ANTIBACTERIAL COMPOSITION FOR CONTROL OF GRAM POSITIVE BACTERIA IN FOOD APPLICATIONS

(75) Inventors: William King, Walnut Creek, CA (US); Xintian Ming, Cottage Grove, WI (US)

(73) Assignee: Rhodia, Inc., Cranbury, NJ (US)

(*) Notice: Subject to any disclaimer, the term of this patent is extended or adjusted under 35 U.S.C. 154(b) by 0 days.

This patent is subject to a terminal disclaimer.

(21) Appl. No.: 10/192,340

(22) Filed: Jul. 10, 2002

(65) Prior Publication Data

US 2002/0197366 A1 Dec. 26, 2002

Related U.S. Application Data

(62) Division of application No. 09/615,972, filed on Jul. 14, 2000, now Pat. No. 6,451,365.

(51) Int. Cl.$^7$ ................................................. A23L 3/36
(52) U.S. Cl. ........................................ 426/335; 426/532
(58) Field of Search ............................. 426/56, 57, 63, 426/310, 324, 323, 326, 335, 532, 574, 618, 580, 600, 614, 615; 424/410, 405, 94.3, 94.61, 195.1, 282.1

(56) References Cited

U.S. PATENT DOCUMENTS

| | | | |
|---|---|---|---|
| 3,932,603 A | | 1/1976 | Haas |
| 4,740,593 A | | 4/1988 | Gonzalez et al. |
| 5,096,718 A | | 3/1992 | Ayres et al. |
| 5,217,950 A | | 6/1993 | Blackburn et al. |
| 5,260,061 A | | 11/1993 | Ayres et al. |
| 5,286,506 A | | 2/1994 | Millis et al. |
| 5,370,863 A | | 12/1994 | Barney et al. |
| 5,455,038 A | | 10/1995 | Barney et al. |
| 5,458,876 A | | 10/1995 | Monticello |
| 5,573,797 A | | 11/1996 | Wilhoit |
| 5,573,800 A | | 11/1996 | Wilhoit |
| 5,573,801 A | | 11/1996 | Wilhoit |
| 6,180,148 B1 | * | 1/2001 | Yajima ........................ 426/392 |

FOREIGN PATENT DOCUMENTS

| | | |
|---|---|---|
| AU | A18604/88 | 1/1989 |
| DE | 3531130 A1 | 3/1987 |
| DE | 19846432 A1 | 4/1999 |
| EP | 0453860 A1 | 10/1991 |
| EP | 0466244 A1 | 1/1992 |
| EP | 0453860 B1 | 6/1994 |
| GB | 2330076 A | 4/1999 |
| JP | 6-098738 * | 4/1994 |
| WO | WO89/00194 | 1/1989 |
| WO | WO96/32482 | 10/1996 |
| WO | WO97/23136 | 7/1997 |
| WO | WO00/38545 | 7/2000 |

OTHER PUBLICATIONS

Foodborne Pathogens: Risk and Consequences, Council for Agricultural Science and Technology, Task Force Report, No. 122, Sep. 1994, pp. 1–87.
Mead et al., Food–Related Illness and Death in the United States, Emerging Infectious Diseases, vol. 5, No. 5, Sep.–Oct. 1999, pp. 607–625.
Larson et al., Antimicrobial activity of hop extracts against *Listeria monocytogenes* in media and in food, International Journal of Food Microbiology 33 (1996) pp. 195–207.
Schnell et al., Prepeptide sequence of epidermin, a ribosomally synthesized antibiotic with four sulphide–rings, Nature, vol. 333, May 1988, pp. 276–278.
Kellner et al., Gallidermin: a new lanthionine–containing polypepetide antibiotic, Eur. J. Biochem. 177 (1988)., pp. 53–59.
Klaenhammer, Bacteriocins of lactic acid bacteria, Biochimie 70 (1988), pp. 337–349.
Proctor, et al., The Chemistry of Lysozyme and its Use as a Food Preservative and a Pharmaceutical, CRC Critical Reviews in Food Science and Nutrition; vol. 26, Issue 4 (1988), pp. 359–395.
Hughey et al., Antimicrobial Activity of Lysozyme against Bacteria Involved in Food Spoilage and Food–Borne Disease, Applied and Environmental Microbiology, Sep. 1987, vol. 53, No. 9, pp. 2165–2170.
CDC 1997 Final Food Net Surveillance Report, U.S. Department of Health and Human Services (available at www.cdc.gov/foodnet/ANNUAL/97_surv.htm).
Doyel, Effect of Environmental and Processing Conditions on *Listeria monocytogenes*, Food Technology, Apr. 1988, vol. 27, pp. 169–171.
Lipinska, Nisin and its Applications, Antibiotics and Antibiosis in Agriculture (Woodbine ed.), Butterworths, pp. 103–130.
Hurst, Nisin, Advances in Applied Microbiology, 1981, vol. 27, pp. 85–123.
Muriana et al., Use of Nisoplin™ to Inhibit Spoilage Bacteria in Buttermilk Ranch Dressing, Journal of Food Protection, 1995, vol. 58, pp. 1109–1113.
Hurst, Nisin and Other Inhibitory Substances from Lactic Acid Bacteria, Food Science, 1983, vol. 10, pp. 327–351.
Buchman et al., Structure, Expression, and Evolution of a Gene Encoding the Precursor of Nisin, a Small Protein Antibiotic, The Journal of Biological Chemistry, 1988, vol. 263, pp. 16260–16266.

* cited by examiner

Primary Examiner—Keith Hendricks
(74) Attorney, Agent, or Firm—Dilworth & Barrese, LLP

(57) ABSTRACT

An antibacterial composition comprising: (a) a first component including at least one gram positive bacteristatic or bactericidal compound selected from the group consisting of: antibiotics, pediocin, and lacticin class bacteriocins, and lytic enzymes; and (b) a second component including at least one compound selected from the group consisting of hops acids, or hops acid derivatives, hops resin; and hops resin derivatives; and the method of applying said composition to the surfaces of solid food.

12 Claims, No Drawings

ANTIBACTERIAL COMPOSITION FOR CONTROL OF GRAM POSITIVE BACTERIA IN FOOD APPLICATIONS

This application is a divisional of U.S. Ser. No. 09/615,972, filed Jul. 14, 2000, now U.S. Pat. No. 6,451,365.

BACKGROUND OF THE INVENTION

1. Field of the Invention

The present invention discloses a process for inhibiting or retarding the outgrowth of bacteria on food products by treatment with a composition which includes one or more hops acid extracts or modified hops acid extracts plus one or more safe and suitable gram positive bacteristatic or bactericidal preparations from the lantibiotics, pediocin, lacticin class bacteriocin and/or lytic enzyme categories. More specifically, the process comprises using as an ingredient or applying to a food surface a composition including nisin, and/or lysozyme and beta hops acids in order to reduce or eliminate gram positive spoilage or pathogenic bacteria, and, most especially, all strains of the harmful pathogen *Listeria monocytogenes*. An important public health concern is the ability of pathogenic listerial species, especially *Listeria monocytogenes*, to grow at commercial refrigeration temperatures at which processed foods are normally stored for long periods of time. This ability to grow under standard conditions of distribution makes *Listeria monocytogenes* one of the top public health risks associated with raw and processed foods today. Any new antimicrobial system must be effective in commercial food systems, with formulation and temperature conditions reflecting actual practices. The new compositions of this patent are effective in a variety of foods, especially at the refrigerated storage and handling temperatures typical of foods at risk for listerial contamination.

2. Technology Description

The extent of food borne infections and intoxications in the United States was quantitatively documented in the CAST report of 1994 (Foodborne Pathogens: Risks and Consequences. Task Force Report No. 122, Council for Agricultural Science and Technology, Washington D.C.), as well as being extensively characterized in the past few years due to better reporting systems and programs (CDC. 1988c. 1997 Final FoodNet Surveillance report. U.S. Department of Health and Human Services, October, 1998). In order to reduce the prevalence of listeriosis and other food borne infections, a wide variety of research has been conducted to develop compositions which function as food grade antibacterial ingredients. Individual compounds have been disclosed in this research, with little if any commercial benefit or use, primarily because single compounds typically lack the efficacy or are too costly to use in food processing and formulations. At this time, there is still a need for better control of gram positive pathogens such as *Listeria monocytogenes, Staphylococcus aureus, Bacillus cereus, Clostridium botulinum, C. perfringens,* and the like, which pose significant health risks to consumers. In addition, other gram positive spoilage bacteria such as lactobacilli, streptococci, bacilli, enterococci, and micrococci species are known to cause spoilage, though not normally illness, and are often the principal agents in reducing the shelf life and freshness of selected foods.

Both pathogenic and spoilage bacteria can occur in raw food materials, but heat processing tends to reduce bacterial loads dramatically. After processing, most foods are at risk for recontamination prior to packaging, distribution, and final consumption, when they may be exposed to pathogens in the food handling environment. Even in the cleanest processing facilities, selected pathogens may contaminate the already processed foods, usually at very low levels. In the case of cold tolerant pathogens, primarily various listerial species, they may then grow unchecked on the food during distribution and storage until final consumption. The more such pathogens grow in a food product, the higher the risk of infection among consumers of that food product. This is a special concern for ready to eat meats and dairy products, as such foods are not heated or processed again by the user prior to consumption. In such cases, the most likely risk is from Listeria species that grow well under refrigeration. Consumption of elevated levels of any pathogen is recognized to increase the risk of infection, especially among infants, the elderly, pregnant women, and any immune compromised individuals.

In 1998, it is estimated that there were approximately 500 deaths in the U.S. caused by listeriosis presumably contracted from foods. Among major food pathogens, listeriosis has the highest mortality, exceeding 20% according to Meade, et al. (Food-related illness and death in the United States, CDC 5:5, September–October 1999). In light of the risk and the large social cost, an urgent need for systems to prevent listerial growth in foods is recognized by U.S. public health agencies, the Food and Drug Administration (FDA), and the United States Department of Agriculture (USDA). The subject of this invention is a novel, food grade (Generally Recognized as Safe), flavor neutral composition that targets Listeria in actual food systems, especially in processed, ready to eat meat products. The desired effect of such a composition is to kill or reduce the levels of Listeria bacteria in foods that are at risk for post processing survival or contamination by such species. In addition, risks associated with other gram positive bacteria, including the above mentioned spoilage types, as well as less common strains of the *Corynebacteria, Diplococci, Mycobacteria, Streptococci*, and *Streptomyces* genuses have also been noted as problems in food-products and may benefit from such a process or composition.

In 1992 and 1993, U.S. Pat. Nos. 5,096,718 and 5,260,061 disclosed the use of metabolites of propionic acid bacteria in certain foods to increase the shelf life of treated food products. These metabolites demonstrate enhanced efficacy against gram negative bacteria but, unfortunately, are not effective against gram positive bacteria.

U.S. Pat. No. 5,217,950 suggested the use of nisin compositions as bactericides. Nisin is a lantibiotic, more specifically, a polypeptide with antimicrobial properties which is produced in nature by various strains of the bacterium *Lactococcus lactis*. Nisin is indeed primarily effective against gram positive bacteria; however, the common gram positive pathogen *Listeria monocytogenes* is more resistant to nisin than most other species of gram positive bacteria. The need to enhance the activity of nisin against *Listeria monocytogenes* is well recognized and accounts for the fact that nisin by itself is not used as an antilisterial agent commercially. The 5,217,950 patent therefore suggests the combination of a chelating agent, such as disodium ethylenediaminetetraacetic acid (EDTA) or other acetate salts or citrate salts with nisin to effect a broader range of activity against both Listeria species as well as selected gram negative bacteria.

U.S. Pat. Nos. 5,573,797; 5,593,800 and 5,573,801 disclose antibacterial compositions which include a combination of a Streptococcus or Pediococcus derived bacteriocin or synthetic equivalent antibacterial agent in combination with a chelating agent. The composition is applied to the surface of the food to be treated either by direct application or by incorporating the composition onto a flexible film casing which is placed into intimate contact with the food surface. The chelating agent binds free divalent cations in the outer membrane of gram negative cells, improving permeability to the antibacterial agents. In the case of the U.S. Pat. No. 5,573,801, the application of nisin alone to the surface of cooked meats is disclosed, but the efficacy of this single ingredient is so limited that it has not been employed commercially.

U.S. Pat. No. 5,458,876 suggests the combination of a antibiotic (such as nisin) with lysozyme as an antibacterial. In this case, lysozyme breaks down the cell wall and weakens the structural integrity of the target cell so that the antibacterial agent becomes more effective in damaging or killing the bacterial cell. In particular, this combination proves to be effective in improving the antibacterial -efficacy of nisin against *Listeria monocytogenes,* yielding a significant reduction, though not a complete elimination, of listeria at safe and suitable levels of use.

EP 0 466 244 discloses a composition having improved antibacterial properties comprising a mixture of at least one of each of the following groups of compounds: (I) a cell wall lysing substance or a salt thereof, (II) an antibacterial compound and (III) an adjuvant selected from organic acids acceptable for use in food products or preparations for cosmetic use or personal hygiene or salts of these acids, phosphates and condensed phosphates or the corresponding acids, and other sequestering agents. Preferably (I) is lysozyme, (II) may be a bacteriocin (e.g. nisin or pediocin), and (III) may be acetic acid, sodium diacetate, lactic acid, citric acid, propionic acid, tartaric acid, orthophosphates, hexametaphosphates, tripolyphosphates, other polyphosphates or sequestering agents containing substituted or non-substituted amino groups, for example EDTA.

EP 0 453 860 suggests the combination of nisin with a phosphate buffer effective at a pH of between 5.5 and 6.5 to eradicate gram negative bacteria from surfaces.

WO 97/23136 suggests a bacterial decontamination method which involves treatment with a solution of low concentration alkali metal orthophosphate combined with either osmotic shock and/or lysozyme in solution and/or nisin in solution. This reference tested the combination of low concentrations of trisodium orthophosphate with lysozyme against certain bacteria on lettuce leaves or chicken skin, and the combination of low concentrations of trisodium orthophosphate with nisin against certain bacteria on chicken skin.

The published Australian patent application AU-A-18604/88 discloses the use of bacteria lysing enzyme products with N-acetylmuramidase, e.g. lysozyme, together with non-enzymatic preservatives for preserving foodstuffs. Non-enzymatic preservatives mentioned in this publication are complexing agents such as citric acid and EDTA, amino acids, particularly amino acids, such as cysteine, alanine, tyrosine and glycine and nucleosides and nucleotides such as inosine 5'-inosine monophosphate or phosphates such as tetrasodiumpyrophosphate (diphosphate), sodium tripolyphosphate (triphosphate) and polyphosphate or reddening agents such as alkali metal nitrates.

U.S. Pat. No. 5,286,506 discloses the use of the fat soluble beta acids extract of hops for their bacteriostatic effects against *Listeria monocytogenes* in foods at 6 to 50 ppm by weight of the food. In addition, U.S. Pat. Nos. 5,370,863 and 5,455,038 suggest that certain hops acid derivatives that are chemically hydrogenated may have antibacterial activity against *listeria* species. However, these extracts are not food grade (GRAS) and are not allowed for use in foods outside of brewing.

Finally, Johnson et al disclose in the International Journal of Food Microbiology 33 (1996) 195–207 that hops acids and hops acid derivatives have limited efficacy against listerial species in fat containing foods such as cheeses, meats, sauces, and dressings, presumably due to the migration or entrapment of the beta acids into the fat emulsion and their subsequent unavailability for inhibition of bacterial growth in the aqueous portion of the food emulsion. The problem of the lack of activity of hop beta acids in fat containing foods has prevented them from being used commercially as natural antimicrobial agents for control of listeria or other gram positive pathogens.

To the extent necessary for completion of this patent application, all of the above cited references are expressly incorporated by reference.

In light of the above teachings, there still exists a need in the art for a method for treating foods with bactericidal compositions that are active at reasonable usage levels in common food applications that are at risk for gram positive pathogens. More specifically, there exists a need for effective treatments that can be conveniently integrated into existing processing protocols for these products. Finally, there exists a need for more complete and effective reduction, or even elimination, of harmful gram positive pathogens by use of safe, suitable, and cost effective levels of food grade anti-microbial ingredients such as nisin, lysozyme, and hops acids.

BRIEF SUMMARY OF THE INVENTION

It is now discovered, quite surprisingly, that a composition which has a first component that includes one or more gram positive bacteristatic or bactericidal compounds from one or more of the following classes of materials: antibiotics, pediocin, and/or lacticin class bacteriocins, or lytic enzymes, and a second component which includes one or more natural hops acids or hops resins or derivatives thereof provides excellent antibacterial properties, especially against potentially harmful bacteria of the listeria genus, by dramatically surpassing the antibacterial efficacy of any of the individual components or of previously published compositions.

One embodiment of the present invention comprises an antibacterial composition containing as a first component: (a) one or more gram positive bacteristatic or bactericidal compounds from one or more of the following classes of materials: lantibiotic, pediocin, and lacticin class bacteriocins, and/or lysozyme, a natural enzyme from egg white; and as a second component (b) one or more hops acids or hops acid derivatives or hops resin or hops resin derivatives. Particularly preferred is a composition containing a lantibiotic bacteriocin, lysozyme, and beta hops acid extract.

In another embodiment, the present invention provides a method for retarding growth, reducing viable numbers, or totally eliminating gram positive bacteria, and especially *Listeria monocytogenes,* in food products comprising the step of treating the surfaces of said food product with an effective amount of a composition comprising as a first component: (a) one or more gram positive bacteristatic or bactericidal compounds from one or more of the following classes of materials: lantibiotics, pediocin and lacticin class bacteriocins, or lytic enzymes; and as a second component (b) one or more hops acid or hops acid derivatives or hops resin or hops resin derivatives.

It is an object of the present invention to provide a process for treating food products in order to protect against harmful bacteria and in order to maintain the antibacterial activity of the composition even on or in a fat containing food.

An additional object of the present invention is to provide a novel composition having substantially greater antibacterial properties than previously observed for the individual components of the composition.

These, and other objects, will readily be apparent to those skilled in the art as reference is made to the detailed description of the preferred embodiment.

DETAILED DESCRIPTION OF THE PREFERRED EMBODIMENT

In describing the preferred embodiment, certain terminology will be utilized for the sake of clarity. Such terminology is intended to encompass the recited embodiment, as well as all technical equivalents which operate in a similar manner for a similar purpose to achieve a similar result.

The present invention provides a novel antibacterial composition and its use in a process for reducing, retarding, or totally eliminating harmful bacteria from food surfaces, even in fat containing foods.

The novel antibacterial composition comprises: (a) one or more gram positive bacteristatic or bactericidal compounds from one or more of the following classes of materials: lantibiotics, pediocin and lacticin class bacteriocins, or lytic enzymes; and (b) one or more hops acid extracts or hops acid derivatives or hops resin or hops resin derivatives.

The first component of the inventive composition is one or more compounds having bacteristatic or bactericidal activity against gram positive bacteria. Such compounds preferably include, but are not limited to lantibiotic, pediocin, and lacticin class bacteriocins and/or lysozyme from egg white, shellfish, or other natural sources. Combinations of more than one compound having bacteristatic or bactericidal activity against gram positive bacteria (e.g., nisin and lysozyme) are specifically contemplated as falling within the more preferred scope of the first component of the present invention.

A first class of gram positive bacteristatic compounds comprises a antibiotic. The term "lantibiotics" was coined by Schnell et al. (1988. Nature 333:276–278) to describe a group of bacteriocins including nisin which contain the amino acid lanthionine and other "non-protein" amino acids. The common properties of these bacteriocins are reviewed by Kellner et al. (1988. Eur. J. Biochem 177:53–59) wherein they note that "... polycyclic polypeptide antibiotics possess a high content of unsaturated amino acids (dehydroalanine, dehydrobutrine) and thioether amino acids (meso-lanthionine, (2S,3S,6R)-3-methyllanthionine). Furthermore, lysinoalanine, 3-hydroxyaspartic acid and S-(2-aminovinyl)-D-cystine are found in some members." Members of this group include nisin, subtilin, pep 5, epidermin, gallidermin, cinnamycin, Ro09-0198, duramycin and ancovenin. These ribosomally synthesized peptide antibiotics contain from 19 to 34 amino acids and are produced by various microbes including Staphlococcus species, lactic acid bacteria, Bacillus species and Streptomyces species. In addition to their unique composition of non-protein amino acids, they can be distinguished from other polypeptide antibiotics on the basis of their specificity. Bacteriocins in general, and the lantibiotics in particular, are characterized by a very narrow spectrum of action. Thus, only a few species of bacteria are sensitive to a particular bacteriocin at practical, safe and suitable concentrations. At normal, legally permitted levels of use in foods (eg., up to 12.5 ppm of pure nisin in a food system), such bacteriocins tend to have only bacteristatic (ie, growth inhibiting) properties at best. This is in contrast with other broad spectrum polypeptide antibiotics, such as polymyxin B1 which are actively bactericidal against a wide range of bacteria, even at very low levels of use, as well as the "lytic peptides" discussed by Jaynes et al., in published international application WO 89/00194, which are active against most bacteria, yeasts and even mammalian cells.

Nisin is a ribosomally coded peptide which occasionally occurs as a dimer with a molecular weight of about 7000. It contains several unusual amino acids including beta-methyllanthionine, dehydroalanine, and lanthionine among its total of 34 amino acids. There are five unusual thio-ether linkages in the peptide which contribute to its stability in acid solutions. Nisin is one of the most thoroughly characterized bacteriocins, and shares remarkable homology of structure and action with other lantibiotics, for example Subtilin and epidermin [Buchman et al 1988. J. Bio. Chem. 263 (31):16260–16266]. Recent reviews of nisin, its physical properties and uses include "Bacteriocins of Lactic Acid Bacteria", T. R. Klaenhammer, 1988. Biochimie 70:337–349, "Nisin", A. Hurst, 1981. Avd. Appl. Microbiol. 27:85–121, and U.S. Pat. No. 4,740,593. Nisin is the collective name describing several closely related substances which exhibit similar amino acid compositions, and some limited range of antibiotic activity. This phenomenon is discussed by E. Lipinska in "Antibiotics and Antibiosis in Agriculture" (M. Woodbine, Ed.) 1988, pp. 103–130.

The use of nisin to combat *L. monocytogenes* has been reported by M. Doyle; "Effect of Environmental and Processing Conditions on *Listeria Monocytogenes*", Food Technology, 1988.42(4):169–171. This reference describes the initial inhibition of the organism's growth (for about 12 hours) and reports that *L. monocytogenes* may grow at a pH level as low as 5.0 and is resistant to alkaline pH with the ability to grow at pH 9.6.

Nisin is commercially available from Rhodia Inc. in a standardized 2.5 weight percent preparation under the trademark Novasin™. Lantibiotic containing protein may also be present as a low level fermentation by-product in certain varieties of cheddar or American cheese and in the fermented skim milk product known as MICROGARD® MG300. In practice the lantibiotic is added to the food product in amounts between about 1 to about 100 ppm (by weight of solution used for treatment) of active ingredient (nisin), with preferred levels of 1 to 12.5 ppm, based on safety and suitability of use in foods.

As alternatives to use of antibiotics in the preferred combination, it is also known that use of a Pediococcus bacterial metabolite, specifically pediocin, as a substitute can yield efficacious results. Though the pediocins are not yet approved for use in foods, they may yet be accepted for commercial application in the future. In addition, the new class of streptococcal bacteriocins called lacticins, especially Lacticin 3147 as described in Irish Patent Application No. 980500, should produce similar activity against gram positive bacteria. Like the lantibiotics, both pediocins and lacticins are known to have bacteristatic activity primarily against a limited range of gram positive bacteria.

A second class of gram positive bactericidal proteins comprises the lytic enzymes especially lysozyme, most commonly derived from egg albumin in a food grade extraction process, but also available from arctic scallops, human milk, tears, and other natural sources. When lysozyme is used as an antimicrobial, it is added to the food product in amounts between about 20 to about 500 ppm (by weight of solution used for treatment), more preferably between about 50 to about 200 ppm, primarily to inhibit *Clostridium tyrobutyricum* in ripened cheeses. Lysozyme is not bactericidal at these levels against other gram positive bacteria, but it has been used at higher levels (greater than 1000 ppm, typically 2000 ppm or more) to remove the cell wall from a wide range of gram positive bacteria.

Lysozymes (Muramidase; mucopeptide N-acetylmucamoylhydrolase; 1,4-.beta.-N acetylhexosaminodase, E.C. 3.2.1.17) are mucolytic enzymes which have been isolated from various sources and are well characterized enzymes. First discovered in 1922 by W. Fleming, egg white lysozyme was among the first proteins sequenced, the first for which a three dimensional structure was suggested using x-ray crystallography and the first for which a detailed mechanism of action was proposed. Its antimicrobial activity against gram positive bacteria is well documented, for example by V. N. Procter et al in CRC Crit. Reviews in Food Science and Nutrition, 1988, 26(4) :359–395. The molecular weight of egg white lysozyme is approximately 14,300 to 14,600, the isoelectric point is pH 10.5–10.7. It is composed of 129 amino acids which are interconnected by four disulfide bridges. Similar enzymes have been isolated and characterized from other sources including such diverse producers as *Escherichia coli* bacteriophage T4 and human tears. Despite slight differences (for example, the human lysozyme has 130 amino acids) the capacity for hydrolysis of acetylhexosamine polymers remains essentially the same. Accordingly, for purposes of this invention, the term lysozyme is intended to include those cell wall or peptidoglycan degrading enzymes which have the ability to hydrolyze acetylhexosamine and related polymers.

Lysozyme is known to kill or inhibit the growth of bacteria and fungi, and is used in Europe to control the growth of the spoilage organism *Clostridium tyrobutyricum* in a wide variety of cheeses. It has also been proposed for use in a variety of other food preservation applications and has been reported to inhibit the growth of (and in some cases kill) *Listeria monocytogenes* (Hughey et al, 1987, Appl. Environ. Microbiol 53:2165–2170). Lysozyme derived from egg albumin with an activity of about 20,000 Shugar units/ mg is commercially available from Rhodia under the trademark NovaGARD™.

In summary, the first component of the novel composition is preferably the previously disclosed combination of lantibiotics and lytic enzymes, especially the more preferred combination of nisin and egg white lysozyme.

The second component of the novel composition is one or more hops acid extracts or hops acid derivatives or hops resins or hops resin derivatives or combinations of some or all of these. The bitter components of the hops used in beer making, particularly the beta-acids, have now been found to be useful as bactericidal agents in food products, particularly in combination with the above mentioned bacteristatic and/ or bactericidal components. The most prevalent groups of bitter acids contained in hops are the alpha-acids and the beta-acids, also referred to as humulones and lupulones, respectively. Both contribute bitterness to beer, but the alpha-acids are much more bitter than the beta-acids and not desirable for use in most food products. Producers of hops extracts isolate the alpha and beta acids commercially by various chromatographic methods and have recently developed a technique to separate the two acid fractions using liquid carbon dioxide under supercritical conditions. A by-product of the operation is a product which contains approximately 61 weight percent beta-acids, the remainder consisting essentially of hops resins. This by-product can be standardized with malto dextrin or other food grade carrier, spray dried, and used as an antibacterial food ingredient. A preferred beta hops acids composition is commercially available as a natural flavor extract containing 1 weight percent beta hops acids.

The alpha-acids contained in hops are commonly known as humulone, cohumulone and adhumulone, while the beta-acids contained in hops are commonly known as lupulone, colupulone and adlupulone. Chemically modified derivatives of hops acids or hops resins which have demonstrated antibacterial properties such as hexahydrocolupulone and tetrahydroisohumulone, as disclosed in U.S. Pat. No. 5,455, 038, are specifically contemplated for use in association with the present invention. Also considered as specifically contemplated for use in association with the present invention is the use of the acid salt forms of the hops acids or hops resins.

In practice, the hops acid or resin or derivatives thereof is added to the food product in amounts between about 0.1 to about 50 ppm of active ingredient (by weight of solution used for treatment), more preferably between about 0.40 to about 20 ppm.

Other additives which can be present in the inventive composition include, but are not limited to the following materials: other antibacterial, such as chitosan or its derivatives, and/or chelating agents, natural or synthetic seasonings, essential oils, and/or flavors, dyes and/or colorants, vitamins, minerals, nutrients, enzymes, binding agents such as guar gum and xanthan gum and the like. In particularly preferred embodiments, guar gum is present in the inventive composition to aid in the binding of the antimicrobial components to the food surface being treated. The addition of these materials is not considered critical to the success of the present invention and would be considered within the skill of the artisan.

The antimicrobial composition of the present invention may be used in connection with any food product which is susceptible to microbial degradation. These include, but are not limited to fruits and vegetables including derived products, grain and grain derived products, dairy foods, meat, poultry, and seafood. In particularly preferred embodiments, the composition is used in connection with meat, poultry and/or seafood, more particularly with fat containing cooked meats such as hotdogs, sausages, roast beef, turkey, corned beef and deli meats.

To reduce the amount of bacteria on a food surface, the novel composition is simply applied to the food surface either before or after cooking. In practice the application of the composition of matter to the food surface may either be a direct application or an indirect application. The use of the term "food surface" is defined to include any and all internal or external surfaces of the food product being treated.

The composition according to the present invention is most readily used by applying it on the exterior surface of a blended food product, such as a hot dog or bologna, or of a solid food, such as a piece of roasted beef, so as to minimize loss of activity in the fat phase of the food. The composition may alternatively be included in the emulsion or raw ingredients of a food such as sauces or salsas, before or after cooking, or to the interior of solid products, such as hams, by injection or tumbling. In still other embodiments, the composition may be applied as a marinade, breading, seasoning rub, glaze, colorant mixture, and the like, the key criteria being that the antimicrobial composition be available to the surface subject to bacterial degradation. In a preferred embodiment, the composition may be indirectly placed into contact with the food surface by applying the composition to food packaging materials or casings and thereafter applying the packaging to the food surface. The use of surface treatment strategies, whether direct or indirect, benefits from the minimization of loss into the fat phase of the fat containing food product. The bacteristatically or bactericidally optimum effective amount to be used will depend on the composition of the particular food product to be treated and the method used for applying the composition to the food surface, but can be determined by simple experimentation.

In a preferred embodiment of this invention, the antibacterial composition comprises from about 38.5 to 99.8 parts by weight of the first component, which includes at least one bacteristatic or bactericidal compound selected from the group consisting of antibiotics, pediocin, lacticin class bacteriocins, and lytic enzymes; to about 61.5 to 0.2 parts by weight of the second component, which includes at least one compound selected from the group consisting of hops acids, hops acid derivatives, hops resins, and hops resin derivatives; all parts by weight being based on the total weight of the first and second components of the composition.

In a more specifically preferred composition embodiment of this invention wherein the first component comprises two compounds, it is preferred that the composition comprises, as a first component, from about 1.0 to 2.5 parts by weight lantibiotic, and from about 37.5 to 97.3 parts by weight lytic enzyme; and as a second component, from about 61.5 to 0,2 parts by weight of at least one compound selected from the group consisting of hops acids, hops acid derivatives, hops resins, and hops resin derivatives; all parts by weight being based on the total weight of the first and second components of the composition.

The following non-limiting examples illustrate the broad range antimicrobial compositions which constitute the present invention.

EXAMPLE 1

As shown in Table 1, two gram positive bacterial strains are tested in Trypticase soy broth, pH 6.0 at 30° C. for 48 hours to show the inhibitory effect of the Novasin™ nisin preparation, lysozyme and beta hops acid either alone or in combination. The test demonstrates the surprisingly synergistic effect of Novasin™, lysozyme and beta hops acid (BHA). Table 1 shows that at the same concentration, the combination of Novasin™, lysozyme and BHA has a significantly better inhibition than the use of each component alone or in two component combinations. The three component combination demonstrates a 5 log reduction of both strains while only 1 to 3 log reduction is observed for any single component treatment or two component treatment.

TABLE 1

|  | CFU/ml | |
| --- | --- | --- |
| Treatment | L. alimentarius | L. monocytogenes |
| Control | 3.1 × 10e8 | 1.4 × 10e8 |
| Novasin (NS) 50 ppm | 5.3 × 10e6 | 7.1 × 10e7 |
| Lysozyme (LY) 50 ppm | 6.3 × 10e6 | 2.5 × 10e7 |
| Beta hops acid (BHA)* 5 ppm | 1.2 × 10e8 | 6.2 × 10e6 |

TABLE 1-continued

|  | CFU/ml | |
| --- | --- | --- |
| Treatment | L. alimentarius | L. monocytogenes |
| NS 50 ppm + LY 50 ppm | 2.5 × 10e5 | 4.1 × 10e6 |
| LY 50 ppm + BHA 5 ppm | 5.6 × 10e6 | 6.3 × 10e6 |
| NS 50 ppm + BHA 5 ppm | 3.5 × 10e5 | 5.2 × 10e5 |
| NS 50 ppm, LY 50 ppm, BHA 5 ppm | 2.8 × 10e3 | 3.1 × 10e3 |

*In this specification, BHA means beta hops acids.

EXAMPLE 2

To demonstrate in vivo efficacy of the inventive composition, hot dogs are inoculated with Listeria monocytogenes. The hot dogs are dipped into suspensions containing either (1) Novasin™, lysozyme and BHA; or (2) Novasin™ and BHA, and then inoculated with L. monocytogenes on the surfaces. The hot dogs are then packed in sterile bags and kept at 10° C. for 13 days. On each sampling day, the hot dogs are rinsed with sterile saline and the resins are plated on Listeria select agar to obtain a Listeria count. Enrichment is performed for the hot dogs by transferring 1 ml of the rinse to BHI broth and incubating for 24 hr, followed by plating on Listeria selective agar. The treatments that have a 0 count on Listeria select agar after enrichment are considered as negative and reported as a fraction of total treated samples.

Table 2 shows that while Novasin™ and BHA dipping significantly reduces the initial levels of Listeria monocytogenes on hot dogs, the three component combination reduces the levels of Listeria monocytogenes to practically undetectable levels, either by direct plating, or by enrichment recovery techniques. In this three component combination there is no observed survival of viable Listeria monocytogenes, as confirmed by the negative results (3/3) after sensitive enrichment techniques that are used to recover low levels of damaged cells. The finding that all of the samples treated with the novel three component combination were negative for Listeria monocytogenes even after enrichment is the most unexpected finding of this application. No such finding has previously been reported using any one of these antimicrobial ingredients at the safe and suitable usage levels described herein.

TABLE 2

|  | CFU/ hot dog | | | Negative after |
| --- | --- | --- | --- | --- |
| Treatment | day-0 | day-2 | day-13 | Enrichment |
| Control | 5 × 10e4 | 1.1 × 10e5 | 9.2 × 10e6 | NA |
| Novasin ™ + BHA | 5 × 10e4 | 30 | 25 | 1/3 |
| Novasin ™ + BHA + lysozyme | 5 × 10e4 | <10 | <10 | 3/3 |

EXAMPLE 3

As shown in Table 3, two gram positive spore formers of the Bacillus genus were tested in Trypticase soy broth, pH 6.0 at 30C. for 48 hours to show the inhibitory effect of the Novasin, lysozyme and beta hops acid either alone or in combination. The test demonstrates the surprisingly synergistic effect of the Novasin, lysozyme and beta hops acid combination against spore formers. Table 3 shows that at the same concentration, the combination of Novasin, lysozyme and BHA shows significantly better inhibition than any ingredient alone or with only two components out of three. The three way combination gives a complete kill of all the inoculated spores, while significant but not complete elimination is observed for single component or two component treatments. Thus, it is here conclusively demonstrated that a composition of Novasin, lysozyme and BHA demonstrates synergistic bactericidal activity against spore forming bacteria.

TABLE 3

| Treatment | CFU/ml | |
| --- | --- | --- |
| | B. subtilis | B. cereus |
| Control | 2.5 × 10e8 | 1.1 × 10e8 |
| 50 ppm Novasin | 3.2 × 10e4 | 6.4 × 10e6 |
| 1 ppm BHA | 360 | 5 × 10e3 |
| 100 ppm Lysozyme | 1.2 × 10e8 | 1.1 × 10e8 |
| 50 ppm Novasin + 1 ppm BHA | 40 | 950 |
| 50 ppm Novasin, 1 ppm BHA and 50 ppm Lysozyme | <10 | <10 |

EXAMPLE 4

Efficacy of the inventive composition for cooked hams is demonstrated in Table 4. Cooked hams were inoculated with *Listeria monocytogenes* on the surface, and then topically treated by spraying the surface with a solution of either Novasin™, lysozyme and BHA (Treatment A); or lysozyme and BHA (Treatment B);. The hams were then shrink wrapped and vacuum packed in sterile bags and stored at 40F. (4° C.) for 60 days. On each sampling day, the hams were rinsed with sterile buffer and the resins were plated on Listeria select agar to determine the viable Listeria count. Enrichment methods were performed for samples with Listeria count below detectable plate count levels by transferring 1 ml of the rinse to brain heart infusion (BHI) broth and incubating for 24 hr, followed by plating on Listeria selective agar. Treatments that had a negative (less than 1/ml) count on Listeria select agar after enrichment are considered as negative and reported as a fraction of total treated samples.

Table 4 shows that the three component combination reduced the inoculated *Listeria monocytogenes* to undetectable levels, either by direct plating, or by enrichment recovery techniques while the control group increased 10,000 fold (4 logs). The two way "lysozyme plus BHA" combination showed inhibition but was not as bactericidal. In the three component combination there is no observed survival of viable *Listeria monocytogenes,* as confirmed by the negative results after enrichment, a technique that is used to recover very low levels of viable or damaged cells. Therefore, the data demonstrate that topical application of the preferred three component composition can completely eliminate *Listeria monocytogenes* in a high fat processed food such as cooked ham.

TABLE 4

| | Listeria counts CFU/ ham pack | | |
| --- | --- | --- | --- |
| Day | Control | Treatment A | Treatment B |
| 1 | 250 | 0 | 50 |
| 7 | 280 | 0 | 200 |
| 15 | 290 | 0 | 160 |
| 30 | 6100 | 0 | 200 |

TABLE 4-continued

| | Listeria counts CFU/ ham pack | | |
| --- | --- | --- | --- |
| Day | Control | Treatment A | Treatment B |
| 45 | 6600 | 0 | 4600 |
| 60 | 20000 | 0 | 5500 |

EXAMPLE 5

Efficacy of the inventive composition for protecting wieners from *Listeria. monocytogenes* is demonstrated in Table 5. The composition of Novasin and BHA was delivered onto the surface of wieners by incorporation of the composition into the cellulosic casing that contains the hotdog emulsion during cooking. After cooking, the casings were peeled off, and then the finished wieners were surface inoculated with *Listeria monocytogenes* and vacuum packed in sterile bags. The packaged, inoculated wieners were stored at 40° F. (4 C.) for over 60 days, with fresh packages opened for each sampling point. At each sampling, the wieners were rinsed along with their package using sterile buffer and the buffer solutions were then plated on Listeria select agar to determine the viable Listeria count.

Table 5 shows that the two component combination inhibited growth of *Listeria monocytogenes* for more than 61 days, and resulted at the end of incubation in a greater than 4 log (10,000 fold) Listeria reduction compared to the controls. The data demonstrate that casing delivered application of the preferred two component composition prevents the outgrowth of *Listeria monocytogenes* on wieners and may be a commercially practical way to deliver the composition and thereby improve the safety of wieners and sausages. More importantly, the surface application method permits the activity of the components to be fully realized, even in the high fat environment of a typical hot dog emulsion. In contrast, antimicrobial activity is dramatically reduced when the composition is employed as an ingredient within the hotdog emulsion prior to cooking (data not shown), consistent with the observations by previous authors that demonstrate the loss of nisin activity (Muriana, P. M. and Kanach, L, Use of Nisaplin to Inhibit Spoilage Bacteria in Buttermilk Ranch Dressing, J. Food Protection, Vol. 58, No 10, 1995) and hops acid activity (Johnson et al., 1996) in foods containing significant fat levels. Therefore, the disclosed method of surface application reveals a surprising way to maximize efficacy of the inventive composition in foods containing elevated fat levels (more than 4% w/w).

TABLE 5

| | Listeria counts log CFU/package | |
| --- | --- | --- |
| Days | Wiener made with control casing | Wiener made with treated casing |
| 0 | 2.72 | 2.72 |
| 7 | 2.51 | 1.8 |
| 27 | 3.66 | 1.92 |
| 33 | 4.3 | 1.84 |
| 40 | 4.34 | 2.23 |
| 54 | 5.48 | 3.43 |
| 61 | 6.83 | 2.08 |

Having described the invention in detail and by reference to the preferred embodiments thereof, it will be apparent that modifications and variations are possible without departing from the scope of the appended claims.

What is claimed is:

1. A food product containing an antibacterial composition consisting essentially of: (a) a first component which is at least one gram positive bacteristatic or bactericidal compound selected from the group consisting of lantibiotics, pediocin, lacticin class bacteriocins, and lytic enzymes; and (b) a second component which is at least one compound selected from the group consisting of beta hops acids and beta hops acid derivatives.

2. The food product of claim 1 wherein the food product contains fat.

3. The food product of claim 2 wherein the food product is a solid containing fat levels of more than 4%.

4. The food product of claim 1 wherein the antibacterial composition is applied to the surface of the food product.

5. The food product according to claim 4 wherein the antibacterial composition has been applied to the surface of the food product by a) coating the composition onto a surface of a casing, film or packaging material, and b) subsequently bringing the composition coated surface into intimate contact with said food product.

6. The food product according to claim 1 wherein the antibacterial composition is included as an ingredient in the food product.

7. A food product containing an antibacterial composition consisting essentially of:
   (a) a first component which is at least one gram positive bacteristatic or bactericidal compound selected from the group consisting of lantibiotics and lytic enzymes; and
   (b) a second component which is at least one compound selected from the group consisting of beta hops acids and beta hops acid derivatives.

8. A food product containing an antibacterial composition consisting essentially of:
   a) nisin;
   b) lysozyme; and
   c) beta hops acids or a beta hops acid derivative.

9. The food product of claim 1 wherein the first component of the antibacterial composition comprises from about 38.5 to 99.8 parts by weight of the antibacterial composition, and the second component of the antibacterial composition comprises from about 61.5 to 0.2 parts by weight of the antibacterial composition.

10. The food product of claim 1 wherein the first component of the antibacterial composition comprises from about 1.0 to 2.5 parts by weight lantibiotic and from about 37.5 to 97.3 parts by weight lytic enzyme, and the second component of the antibacterial composition comprises from about 61.5 to 0.2 parts by weight of at least one compound selected from the group consisting of beta hops acids and beta hops acid derivatives.

11. The food product of claim 1 wherein the food product is selected from the group consisting essentially of fruits, vegetables, fruit-derived products, vegetable derived products, grains, grain derived products, dairy foods, meats, poultry, seafood, sauces and salsas.

12. The food product of claim 1 wherein the food product is selected from the group consisting essentially of cooked meats and cured meats.

* * * * *